US008932809B2

(12) United States Patent
Henkhaus

(10) Patent No.: US 8,932,809 B2
(45) Date of Patent: Jan. 13, 2015

(54) METHODS AND KITS FOR ISOLATING NUCLEIC ACID FROM AN ORGANISM

(75) Inventor: John Kevin Henkhaus, Monona, WI (US)

(73) Assignee: OpGen, Inc., Gaithersburg, MD (US)

(*) Notice: Subject to any disclaimer, the term of this patent is extended or adjusted under 35 U.S.C. 154(b) by 724 days.

(21) Appl. No.: 12/689,270

(22) Filed: Jan. 19, 2010

(65) Prior Publication Data

US 2011/0177521 A1    Jul. 21, 2011

(51) Int. Cl.

| C12Q 1/68 | (2006.01) |
| C07H 21/00 | (2006.01) |
| C07H 21/02 | (2006.01) |
| C07H 21/04 | (2006.01) |
| C12N 1/06 | (2006.01) |
| C12N 15/10 | (2006.01) |

(52) U.S. Cl.
CPC .............. *C12N 1/06* (2013.01); *C12N 15/1003* (2013.01)
USPC ......... 435/6.1; 536/22.1; 536/23.1; 536/24.3; 536/25.4

(58) Field of Classification Search
USPC ............................ 435/6; 536/23.1, 24.3, 25.4
See application file for complete search history.

(56) References Cited

U.S. PATENT DOCUMENTS

| 5,405,519 | A | | 4/1995 | Schwartz | |
| 5,599,664 | A | | 2/1997 | Schwartz | |
| 5,720,928 | A | | 2/1998 | Schwartz | |
| 5,753,467 | A | * | 5/1998 | Jensen et al. | 435/91.2 |
| 6,147,198 | A | | 11/2000 | Schwartz | |
| 6,150,089 | A | | 11/2000 | Schwartz | |
| 6,174,671 | B1 | | 1/2001 | Anantharaman et al. | |
| 6,294,136 | B1 | | 9/2001 | Schwartz | |
| 6,340,567 | B1 | | 1/2002 | Schwartz et al. | |
| 6,448,012 | B1 | | 9/2002 | Schwartz | |
| 6,509,158 | B1 | | 1/2003 | Schwartz | |
| 6,610,256 | B2 | | 8/2003 | Schwartz | |
| 6,713,263 | B2 | | 3/2004 | Schwartz | |
| 6,723,510 | B2 | | 4/2004 | Lubenow et al. | |
| 7,255,989 | B1 | * | 8/2007 | Jeannin et al. | 435/6.1 |
| 7,595,176 | B2 | * | 9/2009 | Loeffler et al. | 435/91.2 |
| 2003/0124611 | A1 | * | 7/2003 | Schwartz | 435/6 |
| 2004/0206208 | A1 | * | 10/2004 | Hunter et al. | 75/743 |
| 2008/0234210 | A1 | * | 9/2008 | Rijn et al. | 514/28 |
| 2010/0143878 | A1 | * | 6/2010 | Olson et al. | 435/2 |
| 2010/0203521 | A1 | * | 8/2010 | Klapperich et al. | 435/6 |
| 2011/0177521 | A1 | * | 7/2011 | Henkhaus | 435/6.15 |

OTHER PUBLICATIONS

Cai et al., Ordered restriction endonuclease maps of yeast artificial chromosomes created by optical mapping on surfaces. PNAS 92 : 5164 (1995).*
Carr et al. Preparative density-gradient ultracentrifugation of DNA. Biochemical Genetics 25 :385 (1987).*
Chen et al., Subtractive hybridization and optical mapping of the enterotoxigenic *Escherichia coli* H10407 chromosome: isolation of unique sequences and demonstration of significant similarity to the chromosome of *E. coli* K-12. Microbiology 152 :1041 (2006).*
Jing et al. Automated high resolution optical mapping using arrayed, fluid-fixed DNA molecules. PNAS 95 : 8046 (1998).*
Latreille et al., Optical mapping as a routine tool for bacterial genome sequence finishing. BMC Genomics 8:321 (2007).*
Moriyon et al., Effects of nonionic, ionic, and dipolar ionic detergents and EDTA on the *Brucella* cell envelope. Journal of Bacteriology 152 (2) : 822 (1982).*
Morozov et al.,New polyacrylamide gel-based methods of sample preparation for optical microscopy: immobilization of DNA molecules for optical mapping. Journal of Microscopy 183 (3) :205 (1996).*
Snailase. OneCoup Lifscience (Jan. 2008).*
Schwartz et al. Separation of yeast chromosome-sized DNAs by pulsed field gradient gel electrophoresis. Cell 37 : 67 (1984).*
Schwartz et al., Ordered restriction maps of *Saccharomyces cerevisiae* chromosomes constructed by optical mapping. Science 262 : 110 (1993).*
Stewart et al., A Rapid CTAB DNA Isolation Technique Useful for RAPD Fingerprinting and Other PCR Applications BioTechniques 14(5):748 (1993).*
Stratagene Catalog p. 39 (1988).*
Weier, H. DNA fiber mapping techniques for the assembly of high-resolution physical maps.\ J. Histochem. & Cytochem. 49, 939-948 (2001).*
Wilson, K. Preparation of genomic DNA fom Bacteria. Unit 2.4 in Current Protocols in Molecular Biology (1997).*
Zhang et al. Synthesis of novel porous magnetic silica microspheres as adsorbents for isolation of genomic DNA. Biotechnology Progress 22 :514 (2006).*
Fishetti, Current Opinion in Microbiology, 11:393-400, 2008.
Young, Microbiol. Rev., 56:430-481, 1992.
Loessner, Curr. Opi. Microbiol., 8:480-487, 2005.
Navarre et al., J. Biol. Chem., 274:15847-15856, 1999.
Nelson et al., Proc Natl Acad Sci USA, 98:4107-4112, 2001.
Loeffler et al., Science, 294:2170-2172, 2001.
Rashel et al., J. Infect. Dis., 196:1237-1247, 2007.
Cheng et al., Antimicrob. Agents Chemother, 49:111-117, 2005.
Harris et al., J. Clin. Invest., 111:61-70, 2003.
Fishetti, Trends in Microb., 13:491-496, 2005.
Robbins et al., J. Bacteriol., 169:5633-5640, 1987.
Loeffler et al., Infect. Immun., 71:6199-6204, 2003.
Yu et al., J. Medical Microbiology, 57:171-178, 2008.
Yoong et al., J. Bacteriol., 186:4808-4812, 2004.
Joong-Sik et al., J. Clin. Microbiology, 1785-1786, 2004.
Kumar et al., Tuberculosis, 88:616-623, 2008.
Marttila et al., Antimicrobial Agents and Chemotherapy, 40:2187-2189, 1996.
Mocz et al., Analytical Biochem., 143(2):283-292, 1984.
Schick, Anal. Biochem., 63(2):345-349, 1975.
Samad et al., Genome Res., 5:1-4, 1995.
Reslewic et al., Appl. Environ. Microbiol., 71(9):5511-22, Sep. 2005.

* cited by examiner

*Primary Examiner* — Ethan Whisenant
(74) *Attorney, Agent, or Firm* — Brown Rudnick LLP; Thomas C. Meyers

(57) ABSTRACT

The invention generally relates to methods and kits for isolating nucleic acids from an organism. In certain embodiments, methods of the invention involve contacting a plurality of lytic enzymes to an organism, thereby lysing a cell wall of the organism to release the nucleic acid, and introducing at least one agent to separate the nucleic acid from the lysed cells, thereby isolating the nucleic acid.

16 Claims, No Drawings

METHODS AND KITS FOR ISOLATING NUCLEIC ACID FROM AN ORGANISM

FIELD OF THE INVENTION

The invention generally relates to methods and kits for isolating nucleic acids from an organism.

BACKGROUND

Physical mapping of genomes, e.g., using restriction endonucleases to develop restriction maps, can provide accurate information about the nucleic acid sequences of various organisms. Restriction maps of, e.g., deoxyribonucleic acid (DNA), can be generated by optical mapping. Optical mapping can produce ordered restriction maps by using fluorescence microscopy to visualize restriction endonuclease cutting events on individual labeled DNA molecules.

In optical mapping, nucleic acid is isolated from an organism, deposited on a substrate, and digested by a restriction enzyme. Methods for isolating nucleic acid from an organism, e.g., bacteria, generally involve embedding cells in agarose followed by gentle lysis via enzymatic and/or chemical digestion of a cell wall of the organism. Agarose protects the nucleic acid from fluid turbulence and other shearing forces that otherwise degrade nucleic acid following lysis. The specific combination of enzymes, digestive chemicals, and/or other procedural variants (e.g., pretreatment of cells) depend on a cell wall composition of a particular organism (e.g., Gram positive or negative).

Those methods pose two concerns for rapidly identifying an organism in clinical samples or in contaminated sources. A first problem is that tailoring a lysis protocol is not possible without previous knowledge of the identity of the organism(s) in the source material. A second problem is that agarose or other semi-solid material is not compatible with fluid flow devices used for nucleic acid deposition.

There is a need for methods and kits for isolating nucleic acids from an organism.

SUMMARY

The invention generally relates to methods and kits for isolating nucleic acids from an organism. Methods of the invention use a plurality of lytic enzymes to lyse a cell wall of an organism and expose nucleic acids of the organism. Because a plurality of different enzymes are used, activity against a broad range of organisms is achieved without needing to know the identity of the organism. Exemplary enzymes include achromopeptidase, lysozyme, lysostaphin, mutanolysin, or a combination thereof.

An agent, such as a cationic detergent or an affinity bead, is used to isolate the nucleic acids from the lysed cells, and a biocompatible polymer is introduced to the isolated nucleic acid. The chosen polymer has a viscosity that allows for the isolated nucleic acids to be used directly in fluid flow applications, such as deposition onto a substrate. Exemplary polymers include methyl cellulose, polyvinylpryollidone (PVP), Ficol, or a combination thereof. In this manner, the isolated nucleic acid remains in a continuously fluid environment, thus maintaining molecular integrity of the nucleic acid, while making the nucleic acids available for subsequent fluid flow applications without the need for additional sample preparation protocols.

Using an enzymatic approach instead of a chemical approach ensures that nucleic acid will not be damaged and/or degraded during the lytic process, as is known to occur during lytic processes that involve chemicals. By abandoning agarose and employing a polymer that increases viscosity of a solution containing the isolated nucleic acid, the nucleic acids are available for subsequent fluid flow applications without the need for additional sample preparation protocols as is required with the use of agarose.

To ensure complete lysis of a cell wall of the organism, methods of the invention may further include introducing proteinase K prior to adding the separating agent. Methods of the invention may also involve isolating the organism from a sample prior to lysing a cell wall of the organism. The sample may be a human tissue or body fluid, an environmental sample, or a food sample.

Once isolated, the nucleic acids may be used for any subsequent analytical process. In a particular embodiment, the isolated nucleic acids are used for optical mapping. The isolated nucleic acid in a solution including a biocompatible polymer are deposited onto a substrate such that the nucleic acid is elongated and fixed on the substrate so that the nucleic acid remains accessible for enzymatic reactions. The nucleic acid is then enzymatically digested to produce one or more restriction digests, which are then imaged. An optical map is then constructed from the restriction digests.

DETAILED DESCRIPTION

The invention generally relates to methods and kits for isolating nucleic acids from an organism, such as an unknown organism. Methods of the invention involve isolating an organism from a sample. The sample may be a human tissue or body fluid. A tissue is a mass of connected cells and/or extracellular matrix material, e.g. skin tissue, nasal passage tissue, CNS tissue, neural tissue, eye tissue, liver tissue, kidney tissue, placental tissue, mammary gland tissue, placental tissue, gastrointestinal tissue, musculoskeletal tissue, genitourinary tissue, bone marrow, and the like, derived from, for example, a human or other mammal and includes the connecting material and the liquid material in association with the cells and/or tissues.

A body fluid is a liquid material derived from, for example, a human or other mammal. Such body fluids include, but are not limited to, mucous, blood, plasma, serum, serum derivatives, bile, blood, maternal blood, phlegm, saliva, sweat, amniotic fluid, mammary fluid, urine, and cerebrospinal fluid (CSF), such as lumbar or ventricular CSF. A sample may also be a fine needle aspirate or biopsied tissue. A sample also may be media containing cells or biological material.

The sample may also be an environmental sample such as water, air, dirt, rock, etc. In other embodiments, the sample is a food sample.

Methods of the invention involve contacting a plurality of lytic enzymes to the organism, thereby providing activity against a broad range of organisms and lysing cells of the organism to release the nucleic acid. Once lysed, at least one agent is introduced to separate the nucleic acid from the lysed cells, thereby isolating the nucleic acid.

In certain embodiments, enzymes are used that have activity against a class of organisms. For example, achromopeptidase has potent bacteriolytic activity for most of the gram-positive aerobic bacteria. Exemplary enzymes that have activity against a class of organisms include achromopeptidase, lysozyme, lysostaphin, mutanolysin, or a combination thereof.

In other embodiments, the enzymes have specificity for a particular organism (known as lysins). Lysins are highly evolved enzymes produced by bacteriophage (phage) to digest the bacterial cell wall for phage progeny release. In Gram-positive bacteria, small quantities of purified recombinant lysin added externally results in immediate lysis causing log-fold death of the target bacterium. Advantages of lysins include specificity for a particular bacteria are shown in (Fishetti, Curr Opi Microbiol, 11:393-400, 2008). A phage lytic enzyme binding to a target bacterium, for example *S. aureus*, and disrupting the cell wall of the bacterium. Once the cell wall is breached, the inner membrane of the bacterium cannot hold the intracellular material and the bacterium bursts, releasing the intracellular material, including intracellular genes and typically gene products, of the bacterium into the sample. The entire process from binding to lysing occurs rapidly, for example, in about 5 seconds, in about 10 seconds, in about 30 seconds, in about 1 minute, in about two minutes, in about three minutes, etc.

Lysins from DNA-phage that infect Gram-positive bacteria are generally between 25 and 40 kDa in size except the PlyC for streptococci that is 114 kDa. This enzyme is unique because it is composed of two separate gene products, PlyCA and PlyCB (Fishetti, Current Opinion in Microbiology, 11:393-400, 2008). With some exceptions, the N-terminal domain contains the catalytic activity of the enzyme. This activity may be either an endo-b-N-acetylglucosaminidase or N-acetylmuramidase (lysozymes), both of which act on the sugar moiety of the bacterial wall, an endopeptidase that acts on the peptide moiety, or an N-acetylmuramoyl-L-alanine amidase (or amidase), which hydrolyzes the amide bond connecting the glycan strand and peptide moieties (Young, Microbiol Rev, 56:430-481, 1992; and Loessner, Curr Opi Microbiol, 8:480-487, 2005). In some cases, particularly staphylococcal lysins, two and perhaps even three different catalytic domains may be linked to a single binding domain (Navarre et al., J Biol Chem, 274:15847-15856, 1999).

Studies of lysin-treated bacteria reveal that lysins exert their effects by forming holes in the cell wall through peptidoglycan digestion (Fishetti, Curr Opi Microbiol, 11:393-400, 2008). The high internal pressure of bacterial cells (roughly 3 to 5 atmospheres) is controlled by the highly cross-linked cell wall. Any disruption in the integrity of the wall will result in extrusion of the cytoplasmic membrane and ultimate hypotonic lysis (Fishetti, Curr Opi Microbiol, 11:393-400, 2008). In certain embodiments, a single enzyme molecule is used to cleave an adequate number of bonds to kill a target bacterium.

In general, lysins only kill the species (or subspecies) of bacteria from which they were produced (Fishetti, Curr Opi Microbiol, 11:393-400, 2008). For instance, enzymes produced from streptococcal phage kill certain streptococci, and enzymes produced by pneumococcal phage kill pneumococci (Nelson et al., Proc Natl Acad Sci USA, 98:4107-4112, 2001; and Loeffler et al. Science, 294:2170-2172, 2001). Specifically, a lysin from a group C streptococcal phage (PlyC) will kill group C streptococci as well as groups A and E streptococci, the bovine pathogen *S. uberis* and the horse pathogen, *S. equi*, without effecting streptococci normally found in the oral cavity of humans and other Gram-positive bacteria (Fishetti, Curr Opi Microbiol, 11:393-400, 2008). Similar results are seen with a pneumococcal specific lysin (Fishetti, Curr Opi Microbiol, 11:393-400, 2008).

An important lysin with respect to infection control is a lysin directed to *S. aureus*. A staphylococcal enzyme and methods of producing the enzyme is described in Fishetti (Curr Opi Microbiol, 11:393-400, 2008) and Rashel et al. (J Infect Dis, 196:1237-1247, 2007). This lysin is easily produced recombinantly and has a significant lethal effect on MRSA both in vitro and in a mouse model (Rashel et al., J Infect Dis, 196:1237-1247, 2007).

Lysins that specifically lyse Group A *Streptococcus* (GAS), vancomycin resistant *Enterococcus* (VRE), *Pneumococcus*, Group B *Streptococcus* (GBS), and *Bacillus anthracis* are also shown in Fishetti (Curr Opi Microbiol, 11:393-400, 2008).

Table 1 below provides phage-lytic enzymes that lyse particular bacteria.

TABLE 1

| Pathogen | Phage Enzyme | References |
|---|---|---|
| MRSA | ClyS | Fishetti, Curr Opi Microbiol, 11: 393-400, 2008 |
| | | Rashel et al., J Infect Dis, 196: 1237-1247, 2007 |
| Group B Strep | PlyGBS | Cheng et al., Antimicrob Agents Chemother, 49: 111-117, 2005 |
| | | Harris et al., J. Clin Invest, 111: 61-70, 2003 |
| Group A Strep | PlyC | Fischetti, Trends in Mocrob, 13: 491-496, 2005 |
| | | Robbins et al., J. Bacteriol., 169: 5633-5640, 1987 |
| Pneumococcus | Cpl-1 | Loeffler et al. Infect Immun, 71: 6199-6204, 2003 |
| | | Yu et al., J. Medical Microbiology, 57: 171-178, 2008 |
| Vancomycin Resistant Enterococcus | PlyV12 | Yoong et al. J. Bacteriol., 186: 4808-4812, 2004 |
| | | Joong-Sik et al. J. Clin Microbiology, 1785-1786, 2004 |
| Bacillus anthracis | PlyG | Fishetti, Curr Opi Microbiol, 11: 393-400, 2008 |
| drug resistant tuberculosis | Che12 | Kumar et al., Tuberculosis, 88: 616-623, 2008 |
| | | Marttila et al. Antimicrobial Agents and Chemotherapy, 40: 2187-2189, 1996 |

Upon lysis of the organism, the intracellular genes or gene products are released. To ensure complete lysis of a cell wall of the organism, methods of the invention may further include introducing proteinase K prior to adding a separating agent.

After lysis, a separating agent is introduced to isolate the nucleic acids from the lysed cells. The separating agent may be a chemical, such as a cationic detergent. Cationic detergents refer to molecules in which an active part of the molecule is a positive ion (cation). Cationic detergents are usually quaternary ammonium salts, such as cetyltrimethylammonium bromide and cetylpyridinium chloride. The cationic detergent is used to facilitate downstream separation of nucleic acid from the lysed cells by electrophoresis. See e.g., Mocz et al. (Analytical Biochem., 143(2):283-292, 1984) and Schick (Anal Biochem., 63(2):345-349, 1975), the contents of each of which are incorporated by reference herein in their entirety.

In other embodiments, the nucleic acid is separated from the lysed cells using affinity beads, such as latex beads, resin beads, magnetic beads, gold beads, polymer beads, or any type of bead known in the art. See e.g., Ni-NTA Magnetic Agarose Beads Handbook, (Qiagen, Hilden, Germany, printed June 1998, distributed August 1998), Lubenow et al. (U.S. Pat. No. 6,723,510), and Sambrook et al. (Molecular Cloning. A Laboratory Manual, 2nd Edition, Cold Spring Harbor Laboratory, New York, 1989), the contents of each of which are incorporated by reference herein in their entirety.

After isolation of the nucleic acid, a biocompatible polymer is added to a solution including the isolated nucleic acid. The chosen polymer has a viscosity that allows for the isolated nucleic acids to be used directly in fluid flow applications, such as deposition onto a substrate. Exemplary polymers include methyl cellulose, polyvinylpryollidone (PVP), Ficol, or a combination thereof. In this manner, the isolated nucleic acid remains in a continuously fluid environment, thus maintaining molecular integrity of the nucleic acid, while making the nucleic acids available for subsequent fluid flow applications without the need for additional sample preparation protocols.

Once isolated, the nucleic acids may be used for any subsequent analytical process. In a particular embodiment, the isolated nucleic acids are used for optical mapping. Optical mapping is a single-molecule technique for production of ordered restriction maps from a single DNA molecule (Samad et al., *Genome Res.* 5:1-4, 1995). Various methods can be used for controllable elongation of single nucleic acid molecules in optical mapping and/or sequencing. The methods can be gel-based, solid surface-based, and flow-based (see, e.g., U.S. Pat. No. 6,509,158). During some applications, individual fluorescently labeled DNA molecules are elongated in a flow of agarose between a coverslip and a microscope slide (in a first-generation method) or fixed onto polylysine-treated glass surfaces (in a second-generation method). Samad et al. supra. The added endonuclease cuts the DNA at specific points, and the fragments are imaged. Id. Restriction maps can be constructed based on the number of fragments resulting from the digest. Id. Generally, the final map is an average of fragment sizes derived from similar molecules. Id.

Optical mapping and related methods are described in U.S. Pat. No. 5,405,519, U.S. Pat. No. 5,599,664, U.S. Pat. No. 6,150,089, U.S. Pat. No. 6,147,198, U.S. Pat. No. 5,720,928, U.S. Pat. No. 6,174,671, U.S. Pat. No. 6,294,136, U.S. Pat. No. 6,340,567, U.S. Pat. No. 6,448,012, U.S. Pat. No. 6,509, 158, U.S. Pat. No. 6,610,256, and U.S. Pat. No. 6,713,263. All the cited patents are incorporated by reference herein in their entireties.

Optical Maps are constructed as described in Reslewic et al., Appl Environ Microbiol. 2005 September; 71 (9):5511-22, incorporated by reference herein. Briefly, individual chromosomal fragments from test organisms are immobilized on derivatized glass by virtue of electrostatic interactions between the negatively-charged DNA and the positively-charged surface, digested with one or more restriction endonuclease, stained with an intercalating dye such as YOYO-1 (Invitrogen) and positioned onto an automated fluorescent microscope for image analysis. Since the chromosomal fragments are immobilized, the restriction fragments produced by digestion with the restriction endonuclease remain attached to the glass and can be visualized by fluorescence microscopy, after staining with the intercalating dye. The size of each restriction fragment in a chromosomal DNA molecule is measured using image analysis software and identical restriction fragment patterns in different molecules are used to assemble ordered restriction maps covering the entire chromosome.

Restriction mapping, e.g., optical mapping, can be used in a variety of applications. For example, the methods featured herein can be used to determine a property, e.g., physical and/or chemical property, e.g., size, length, restriction map, weight, mass, sequence, conformational or structural change, pKa change, distribution, viscosity, rates of relaxation of a labeled and/or non-labeled molecule, e.g., an amplicon (e.g., PCR product), of a portion of a genome (e.g., a chromosome), or of an entire genome.

The methods can also be used to identify various organisms, e.g., viruses and prions, and various microorganisms, e.g., bacteria, protists, and fungi, whose genetic information is stored as DNA or RNA by correlating the restriction map of a nucleic acid of an organism with a restriction map database. Such identification methods can be used in diagnosing a disease or disorder. Methods of identifying organisms by restriction mapping are described, e.g., in a U.S. patent application Ser. No. 12/120,586, filed on May 14, 2008, incorporated herein by reference.

The methods featured herein can also be used in other diagnostic applications, for example, imaging specific loci or genetic regions for individuals or populations to help identify specific diseases or disorders. Other uses of the methods will be apparent to those skilled in the art.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A method for isolating nucleic acid from an organism, the method comprising:
   lysing a cell wall of an organism using a composition comprising a plurality of lytic enzymes and that does not contain non-protein lysing chemicals, thereby releasing nucleic acid from the organism;
   introducing at least one agent to separate the nucleic acid from the lysed organism, thereby isolating the nucleic acid; and
   introducing at least one liquid biocompatible polymer to the isolated nucleic acid, wherein the biocompatible polymer has a viscosity that allows for the isolated nucleic acids to be used in fluid flow applications, with the proviso that the polymer is not agarose.

2. The method according to claim 1, wherein prior to introducing the agent, the method further comprises introducing proteinase K.

3. The method according to claim 1, wherein the agent is a cationic detergent.

4. The method according to claim 1, wherein the agent is an affinity bead.

5. The method according to claim 4, wherein the affinity bead is a magnetic bead.

6. The method according to claim 1, wherein prior to the contacting step, the method further comprises separating the organism from a sample.

7. The method according to claim 6, wherein the sample is selected from the group consisting of a human tissue or body fluid, an environmental sample, and a food sample.

8. The method according to claim 1, wherein the plurality of lytic enzymes are selected from the group consisting of achromopeptidase, lysozyme, lysostaphin, mutanolysin, and a combination thereof.

9. The method according to claim 1, wherein the organism is an unknown organism.

10. The method according to claim 1, wherein lysis occurs in solution.

11. A method for generating a physical map of a genome of an organism, the method comprising:
- contacting an organism with a composition comprising a plurality of lytic enzymes but no non-protein lysing chemicals in order to lyse a cell wall of the organism, thereby releasing nucleic acid from the organism;
- introducing at least one agent to separate the nucleic acid from the lysed organism, thereby isolating the nucleic acid;
- introducing at least one liquid biocompatible polymer to the isolated nucleic acid, wherein the biocompatible polymer has a viscosity that allows for the isolated nucleic acids to be used in fluid flow applications, with the proviso that the polymer is not agarose;
- depositing the nucleic acid onto a substrate such that the nucleic acid is elongated and fixed on the substrate so that the nucleic acid remains accessible for enzymatic reactions;
- digesting the nucleic acid enzymatically to produce one or more restriction digests;
- imaging the restriction digests; and
- constructing an optical map from the restriction digests.

12. The method according to claim 11, wherein prior to introducing the agent, the method further comprises introducing proteinase K.

13. The method according to claim 11, wherein prior to the contacting step, the method further comprises separating the organism from a sample.

14. The method according to claim 11, wherein lysis occurs in solution.

15. The method according to claim 11, wherein the agent is a cationic detergent.

16. The method according to claim 11, wherein the agent is an affinity bead.

* * * * *